United States Patent [19]

Wollensak et al.

[11] 4,341,903

[45] * Jul. 27, 1982

[54] PROCESS FOR REARRANGEMENT OF ALKYL GROUPS ON AROMATIC AMINES

[75] Inventors: John C. Wollensak, Bloomfield Hills; Kryn G. Ihrman, Farmington; Chester P. Jarema, Sterling Heights, all of Mich.

[73] Assignee: Ethyl Corporation, Richmond, Va.

[*] Notice: The portion of the term of this patent subsequent to Mar. 2, 1999, has been disclaimed.

[21] Appl. No.: 253,099

[22] Filed: Apr. 13, 1981

Related U.S. Application Data

[63] Continuation-in-part of Ser. No. 240,752, Mar. 5, 1981, Pat. No. 4,317,931, which is a continuation-in-part of Ser. No. 72,931, Sep. 6, 1979, abandoned.

[51] Int. Cl.$^3$ ............................................. C07C 85/24
[52] U.S. Cl. ............................................. 564/409
[58] Field of Search ........................................ 564/409

[56] References Cited

U.S. PATENT DOCUMENTS

| | | | |
|---|---|---|---|
| 1,844,518 | 2/1932 | Minnis | 564/409 |
| 2,814,646 | 11/1957 | Kolka et al. | 564/409 |
| 3,275,690 | 9/1966 | Stroh et al. | 564/409 |
| 3,417,149 | 12/1968 | Neuworth et al. | 568/804 |
| 3,418,380 | 12/1968 | Laufer et al. | 568/784 |
| 3,649,693 | 3/1972 | Napolitano | 564/409 |
| 3,654,331 | 4/1972 | Klopfer | 564/409 X |
| 3,674,852 | 7/1972 | Averill et al. | 564/409 |
| 3,759,997 | 9/1973 | Napolitano | 564/409 X |
| 3,761,520 | 9/1973 | Napolitano | 564/409 |
| 3,923,892 | 12/1975 | Klopfer | 564/409 |
| 3,933,927 | 1/1976 | Goddard | 568/780 |
| 4,128,582 | 12/1978 | Governale et al. | 564/409 |

OTHER PUBLICATIONS

Kirk-Othmer, "Encyclopedia of Chemical Technology," vol. 5, 2nd Ed., pp. 740 and 744, (1964), vol. 20, 2nd Ed., p. 486, (1965).

Groggins, "Unit Processes in Organic Synthesis," 5th Ed., p. 807, (1958).

Ogata et al., "Chemical Abstracts," vol. 62, pp. 2687–2688, (1965).

Olah, "Friedel-Crafts and Related Reactions," vol. II, Part 1, pp. 531–533, (1964).

*Primary Examiner*—Robert V. Hines
*Attorney, Agent, or Firm*—Donald L. Johnson; Joseph D. Odenweller; John F. Hunt

[57] ABSTRACT

Methyl groups on N-methyl aromatic amines are redistributed to ring positions by heating in contact with an aluminum anilide catalyst and a nickel, cobalt, molybdenum or titanium-containing cocatalyst. For example, N-methyl-o-toluidine forms a mixture containing substantial quantities of 2,6-dimethylaniline, 2,4-dimethylaniline, and 2,4,6-trimethylaniline.

11 Claims, No Drawings

PROCESS FOR REARRANGEMENT OF ALKYL GROUPS ON AROMATIC AMINES

CROSS REFERENCE TO RELATED APPLICATIONS

This application is a continuation-in-part of application Ser. No. 240,752, and now U.S. Pat. No. 4,317,931 filed Mar. 5, 1981, which in turn is a continuation-in-part of application Ser. No. 072,931, filed Sept. 6, 1979, now abandoned.

BACKGROUND OF THE INVENTION

Aromatic amines can be alkylated selectively in an ortho position by reaction with an olefin in the presence of an aluminum anilide catalyst. Such reactions are described in Kolka et al, U.S. Pat. No. 2,814,646; Stroh et al, U.S. Pat. No. 3,275,690; Klopfer, U.S. Pat. No. 3,923,892 and Governale et al, U.S. Pat. No. 4,128,582. It is also known that tert-alkyl groups on phenols can be redistributed using sulfuric acid catalysts, cf U.S. Pat. No. 3,418,380. Similarly, methyl groups on phenols have been redistributed using an alumina catalyst, cf U.S. Pat. No. 3,417,149. Transalkylation of phenol by sec-alkyl and tert-alkyl phenols using an aluminum phenoxide catalyst is described in U.S. Pat. No. 3,933,927.

The prior art has not shown, however, how to methylate anilines in the ortho or other ring positions since no olefin can provide a methyl group.

SUMMARY

According to the present invention, o-methyl groups on o-methyl aromatic amines are redistributed to unsubstituted positions on aromatic amines by heating the o-methyl aromatic amine in the presence of an aluminum anilide-type catalyst and a metal-containing cocatalyst wherein the metal is nickel, cobalt, molybdenum or titanium.

Although it is an object of this invention to form 2,6-dimethylaniline, it has been found that varying proportions of both 2,6- and 2,4-dimethylaniline are formed by the inventive process depending on the catalysts, starting material used, as well as the type of reaction vessel.

Also, according to the present invention, ring methylated anilines are provided from N-methyl and N,N-dimethyl anilines. There is apparently both intra- and inter-molecular migration of methyl groups.

DESCRIPTION OF THE PREFERRED EMBODIMENTS

A preferred embodiment of the invention is a process for redistributing methyl groups on nuclear methyl-substituted aromatic amines, said process comprising heating an aromatic amine or mixture of aromatic amines, said aromatic amine or mixture of aromatic amines containing (a) aromatic amine having at least one o-methyl substituent and (b) aromatic amine having at least one ortho position unsubstituted except for hydrogen, at a temperature of about 100°-500° C. in the presence of an aluminum anilide catalyst and a metal-containing cocatalyst, said metal being selected from nickel, cobalt, molybdenum and titanium.

Another preferred embodiment of the invention is a process for producing nuclearly (ring) methyl-substituted anilined from N-methyl substituted anilines by heating an N-methyl substituted aniline or a mixture of such anilines at a temperature of about 100°-500° C. in the presence of an aluminum anilide catalyst and a metal-containing cocatalyst, said metal being selected from nickel, cobalt, molybdneum, and titanium. For this embodiment, N-methyl-o-toluidine is a more preferred starting material; nickel is an especially preferred metal; and about 350° C. is a more preferred process temperature.

The aromatic amines which are subject to the redistribution reaction can be a single aromatic amine or a mixture of aromatic amines. If it is a single aromatic amine it must have an o-methyl substituent and an unsubstituted ortho position. Other positions may be unsubstituted or substituted with groups such as alkyl, halide and the like. When using a single aromatic amine the preferred compound is o-toluidine. When heated in the presence of an aluminum anilide-type catalyst and a nickel, cobalt, molybdenum or titanium containing cocatalyst, o-toluidine redistributes methyl groups according to the following reaction:

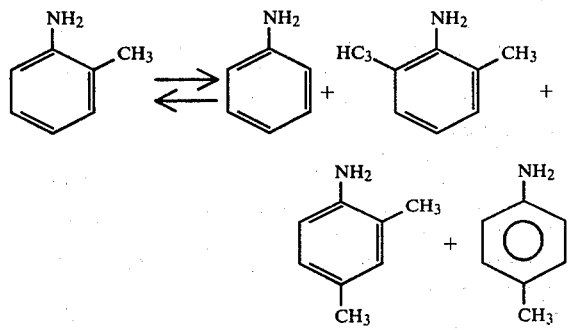

The equilibrium for the reaction favors o-toluidine. However, aniline may be distilled out shifting the equilibrium to the right, increasing the formation of 2,6-dimethylaniline and 2,4-dimethylaniline.

In the event that 2,6-dimethylaniline is in good supply, it can be used as a source of methyl groups to be redistributed to the other aromatic amines having unsubstituted ortho positions. Examples of aromatic amines having unsubstituted ortho positions are aniline, o-ethylaniline, α-naphthylamine, β-naphthylamine, p-chloroaniline and the like.

Tri-substituted aniline can be used as a source of methyl groups. An example of such a donor compound is 2,4,6-trimethylaniline. In this case, the p-methyl group does not migrate to any extent.

Normally, 2,6-dimethylaniline is not in good supply and another embodiment of the invention redistributes methyl groups in fair yields according to the following reaction:

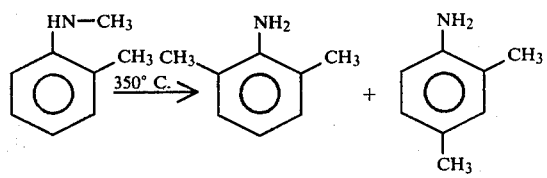

Examples of suitable starting materials are N-methyl-o-toluidine, N-methylaniline, and N,N-dimethylaniline.

Aluminum anilide-type catalysts useful in the process include those used to ortho alkylate aromatic amines as described in U.S. Pat. No. 2,814,646; U.S. Pat. No. 3,275,690; U.S. Pat. No. 3,923,892 and U.S. Pat. No. 4,128,582.

The aluminum trianilides are readily made by reacting aluminum metal, aluminum hydride, or aluminum tri-lower alkyl such as triisobutyl aluminum with an aromatic amine. This can be carried out by adding the aluminum or aluminum compound to the aromatic amine and heating under a nitrogen atmosphere until an exothermic reaction occurs. This is conducted in an autoclave which can withstand at least 1000 psig. When aluminum alkyls are used to prepare the catalyst care should be taken in handling these materials because of their pyrophoric nature. Aluminum alkyls react with aromatic amines at fairly low temperatures from about ambient temperature up to about 150° C. Aluminum metal generally requires heating the mixture to about 200°–300° C. Once the catalyst formation starts it proceeds rapidly. Examples of aluminum trianilide are aluminum trianilide, aluminum tri-(2-methylanilide), aluminum tri-(p-chloroanilide), aluminum tri-(2,4-dimethylanilide) and the like.

A second class of aluminum anilide-type catalysts are the above aluminum trianilides in combination with a Friedel-Crafts promoter such as aluminum chloride, aluminum bromide, stannic choride, boron trifluoride and the like.

A third class of aluminum anilide-type catalysts are the catalysts formed by reacting an alkyl aluminum halide with an aromatic amine. Suitable alkyl aluminum halides for forming the catalysts are diethyl aluminum chloride, ethyl aluminum dichloride, ethyl aluminum sesquichloride, methyl aluminum sesquichloride and the like.

A fourth type of aluminum anilide-type catalysts are the hydrogen halide promoted aluminum anilides. In this class a hydrogen halide is added to the previously described aluminum trianilide-type catalyst to promote the catalyst. Of the hydrogen halides, hydrogen chloride is preferred. An amount sufficient to provide about 0.1–2 gram atoms of chloride per gram atom of aluminum is a useful ratio.

The amount of aluminum anilide-type catalyst added to the aromatic amine can vary over a wide range. A useful range is that amount which provides about 0.005–0.5 gram atom of aluminum per mole of aromatic amines. A more preferred range is about 0.1–0.25 gram atom of aluminum per mole of aromatic amine.

The metal-containing cocatalysts are those which contain nickel, cobalt, molybdenum or titanium. Examples of these are nickel carbonate, cobalt naphthenate, molybdenum naphthenate and titanium tetraalkoxide such as tetraisopropoxide, tetrabutoxide, tetradecoxide and the like. Other representative examples of these cocatalysts are nickel chloride, nickel bromide, nickel sulfate, nickel dibutyldithiocarbonate, cobaltic chloride, titanium trichloride, titanium tetrachloride, nickel naphthenate, nickel acetate, nickel oleate, nickel metal, cobaltic acetate, cobaltous bromide, cobaltous oxalate, cobalt metal, titanium bromide and the like.

The amount of cocatalysts can vary over a wide range. A useful concentration is that which provides about 0.005–0.5 moles per mole of aromatic amine. A more preferred range is 0.01–0.02 mole of aromatic amine.

The redistribution reaction is carried out by adding the catalyst precursor to the o-methyl or N-methyl aromatic amine or mixture of aromatic amines as previously described. This is heated under nitrogen to form the aluminum anilide catalyst prior to adding the metal cocatalyst or the metal cocatalyst can be added prior to heating. In either event, the heating is conducted under an inert atmosphere such as nitrogen in a sealed autoclave. After the aluminum anilide-type catalyst forms the autoclave is cooled and vented although venting is not required. The autoclave is then sealed and heated to reaction temperature. An elevated temperature is required. A useful range for carrying out the redistribution reaction is about 200°–500° C. A preferred temperature range is about 300°–400° C.

The following examples serve to illustrate the manner in which the process is conducted.

At the time the following experimental examples were run, it was thought that 2,6-dimethylaniline was formed without the production of 2,4-dimethylaniline. Further studies and additional analysis techniques have indicated the presence of 2,4-dimethylaniline as a minor proportion of the dimethylaniline formed. In the following examples, only "dimethylaniline" content of the reaction product is reported. In examples 1–6 the proportion of 2,6- to 2,4-dimethylaniline is about 1:2. That ratio varies with reactants, their purity, the catalyst, and the reaction vessel.

EXAMPLE 1

In an autoclave was placed 107.2 grams of o-toluidine, 4.6 grams aluminum granules and 0.99 gram nickel carbonate. The autoclave was flushed with nitrogen and heated to 300° C. An exothermic reaction occurred indicating catalyst formation. Heating was continued to 350° C. and the reaction was held at 350° C. with stirring for 4.25 hours. Pressure was 890 psig. The reaction was then cooled, vented and analyzed by vapor phase chromatography (VPC) to contain 23% aniline, 71% o-toluidine, and 5.9% dimethylaniline. These products can be separated by distillation.

EXAMPLE 2

In an autoclave was placed 107.2 grams of o-toluidine and 1.2 grams nickel carbonate. The autoclave was flushed with nitrogen and then 22.6 grams (27 ml) of triethyl aluminum was added. The autoclave was sealed and heated. At 150° C. a pressure jump was observed indicating catalyst formation. The autoclave was cooled and vented. It was again sealed and heated rapidly to 150° C. and slowly to 350° C. It was stirred at 350° C. for 1 hour following which a sample was removed and analyzed by VPC. Its composition was 20.3% aniline, 69.3% o-toluidine, 3.3% dimethylaniline and 7.6% high boiling products.

EXAMPLE 3

In an autoclave was placed 107.2 grams of o-toluidine, 5.4 grams aluminum granules and 5.3 grams molybdenum naphthenate. The autoclave was flushed with nitrogen, sealed, and while stirring, heated to 330° C. over one hour. It was stirred at 330° C. for 35 minutes and then cooled and vented. It was resealed and heated to 330° C. and maintained at that temperature for 22 hours. It was then cooled and the product analyzed by VPC. It contained 1% aniline, 95% o-toluidine, and 4% dimethylaniline.

EXAMPLE 4

In an autoclave was placed 107.2 grams of o-toluidine, 5.4 grams aluminum granules and 3.4 grams titanium tetrabutoxide. The autoclave was flushed with nitrogen, sealed and heated to 330° C. Pressure rose to 840 psig. It was cooled and vented to remove a sample. It was sealed and reheated to 330° C. and stirred at that temperature for about 5 hours. It was then cooled and vented and analyzed by VPC. It contained 0.5% aniline, 91% o-toluidine, 2.6% dimethylaniline and 5.7% toluene.

EXAMPLE 5

In an autoclave was placed 107.2 grams of o-toluidine, 5.4 grams aluminum granules and 10 grams cobalt naphthenate (0.6 g cobalt). The autoclave was sealed and heated to 330° C. causing a pressure jump to 860 psig. The autoclave was cooled and vented. It was resealed and heated to 330° C. and stirred at that temperature for 18.5 hours. It was then cooled and vented and the product analyzed by VPC. It contained 8.7% aniline, 53.8% o-toluidine, 8.6% dimethylaniline and 7.4% high boiling products.

EXAMPLE 6

In an autoclave was placed 107.2 grams o-toluidine and 5.4 grams aluminum granules. The autoclave was flushed with nitrogen and heated to 330° C. The temperature jumped to 380° C. at 800 psig. The autoclave was stirred for 30 minutes at 330° C. and then cooled and vented. Then 10 grams of cobalt naphthenate (0.6 gram cobalt) was added and the autoclave again heated to 330° C. It was stirred at that temperature for 2 hours following which it was cooled and vented. It was sealed and reheated to 330° C. and stirred at that temperature for 2 hours. It was then cooled, vented and discharged. A strong ammonia odor was noted. Analysis by VPC showed benzene 7%, toluene 8%, aniline 15%, o-toluidine 48%, and dimethylaniline 16%.

The aromatic amines made by this process are useful chemicals. One important use is as an intermediate in the production of herbicides and fungicides such as those described in U.S. Pat. No. 3,853,531; U.S. Pat. No. 3,859,308; U.S. Pat. No. 3,885,952; U.S. Pat. No. 3,888,882; U.S. Pat. No. 4,001,325 and U.S. Pat. No. 4,025,554.

EXAMPLE 7

In a 600 ml autoclave was placed 214.4 grams (2.0 moles) N-methylaniline and 2.4 grams (0.02 mole Ni) nickel carbonate, NiCO$_3$. The autoclave was flushed and pressure tested with nitrogen before adding 45.2 grams (54 ml.) of triethylaluminum over a thirty-minute period. The autoclave was sealed and heated at 150° C. for about 30 minutes whereupon a pressure jump was observed, indicating catalyst formation. Thereafter, a pressure of 400–500 psi developed which was vented after cooling to room temperature. The autoclave was then heated for 2-3 hours at 350° C. Complete analysis by capillary vapor phase chromatography disclosed the following composition:

| Component | Area % |
| --- | --- |
| 2,6-dimethylaniline | 1.1 |
| 2,4-dimethylaniline | 8.1 |
| 2,4,6-trimethylaniline | 0.5 |
| N,N-dimethylaniline | 0.3 |
| N-methylaniline | 5.4 |
| N-methyl-o-toluidine | 0.4 |
| Aniline | 42.6 |
| o-toluidine | 11.1 |
| p-toluidine | 27.7 |
| Others | 2.8 |

Of course, the N-methyl substituted components may be recycled in the process. The aniline and toluidines can be used in the other embodiment of this invention.

EXAMPLE 8

In a 600 ml autoclave was placed a mixture of 218.2 grams (1.8 moles) N,N-dimethylaniline, 21.4 grams (0.2 mole) N-methylaniline, and 2.4 grams (0.02 mole Ni) nickel carbonate, NiCO$_3$. The autoclave was flushed and pressure tested with nitrogen before adding 45.2 grams (54 ml., 0.4 mole) triethylaluminum over a thirty-minute period. The autoclave was sealed and heated to about 300° C. for 30 minutes whereupon a pressure of 754 psi developed, indicating catalyst formation. The autoclave was then cooled to room temperature and vented. After resealing, the autoclave was heated to 350° C. and maintained at that temperature for about seven hours. Periodic samples were taken during the seven-hour heating period to follow the reaction progress until complete. Analysis by capillary vapor phase chromatography gave the following composition:

| Component | Area % |
| --- | --- |
| 2,6-dimethylaniline | 2.4 |
| 2,4-dimethylaniline | 30.4 |
| 2,4,6-trimethylaniline | 13.7 |
| N,N-dimethylaniline | 0.5 |
| N-methylaniline | 0.8 |
| N-methyl-o-toluidine | 0.5 |
| N-methyl-p-toluidine | 0.4 |
| o-toluidine | 7.2 |
| p-toluidine | 23.4 |
| Aniline | 8.0 |
| Unknowns | 9.1 |

EXAMPLE 9

In a 600 ml autoclave was placed 60.5 grams (0.5 mole) N-methyl-o-toluidine, 100 grams ethylbenzene solvent, and 0.6 grams (0.005 mole Ni) nickel carbonate, NiCO$_3$. The autoclave was flushed and pressure checked with nitrogen before adding 11.3 grams (14 ml, 0.1 mole) triethylaluminum over a 30-minute period. The autoclave was sealed and heated to about 150° C. for about 40 minutes whereupon a pressure jump was observed, indicating catalyst formation. The autoclave was cooled to room temperature and vented. After resealing, the autoclave was heated to 350° C. and maintained at that temperature for about 2½ hours before slowly cooling to room temperature and venting. Analysis disclosed the presence of several unknowns and heavy ends plus the following:

| Component | Area % |
| --- | --- |
| 2,6-dimethylaniline | 14.14 |
| 2,4-dimethylaniline | 20.43 |
| 2,4,6-trimethylaniline | 8.00 |
| Aniline | 1.37 |
| N-methyl-o-toluidine | 7.28 |
| p-toluidine | 1.60 |

| Component | Area % |
|---|---|
| o-toluidine | 29.88 |

Various permutations of the above experiments qualified the process temperature range, workable catalysts and cocatalysts, and the appropriate reaction aromatic amines or mixtures thereof. The above examples are non-limiting and the invention may be practiced by varying certain features thereof without departing from the scope or spirit of the invention as defined by the following claims:

We claim:

1. A process for producing nuclearly methyl-substituted anilines from N-methyl substituted anilines comprising heating an N-methyl substituted aniline at a temperature of about 100°–500° C. in the presence of an aluminum anilide catalyst and a metal-containing cocatalyst, said metal being selected from nickel, cobalt, molybdenum, and titanium.

2. The process of claim 1 wherein said N-methyl substituted aniline is N,N-dimethylaniline.

3. The process of claim 2 wherein N-methylaniline is also present as about 10 mole percent of the total N-methyl substituted aniline.

4. The process of claim 1 wherein said N-methyl substituted aniline is N-methyl-o-toluidine.

5. The process of claim 1 wherein said aluminum anilide catalyst is formed from triethyl aluminum and an N-methyl substituted aniline.

6. The process of claim 1 wherein said metal is nickel.

7. The process of claim 6 wherein said cocatalyst is nickel carbonate, $NiCO_3$.

8. The process of claim 6 wherein said cocatalyst is nickel dibutyldithiocarbamate.

9. The process of claim 1 wherein said aluminum anilide catalyst is formed from diethyl aluminum chloride and an N-methyl substituted aniline.

10. The process of claim 1 wherein said aluminum anilide catalyst is formed from triisopropyl aluminum and an N-methyl substituted aniline.

11. The process of claim 1 wherein said temperature is about 350° C.

* * * * *